United States Patent
Schleipen et al.

(10) Patent No.: US 8,670,123 B2
(45) Date of Patent: Mar. 11, 2014

(54) OPTICAL BIOSENSOR WITH FOCUSING OPTICS

(75) Inventors: Johannes Joseph Hubertina Barbara Schleipen, Eindhoven (NL); Dominique Maria Bruls, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 63 days.

(21) Appl. No.: 13/379,721

(22) PCT Filed: Jun. 21, 2010

(86) PCT No.: PCT/IB2010/052786
§ 371 (c)(1),
(2), (4) Date: Mar. 1, 2012

(87) PCT Pub. No.: WO2010/150167
PCT Pub. Date: Dec. 29, 2010

(65) Prior Publication Data
US 2012/0147377 A1    Jun. 14, 2012

(30) Foreign Application Priority Data
Jun. 24, 2009    (EP) .................................... 09163571

(51) Int. Cl.
*G01N 21/55*    (2006.01)
*G02B 3/00*    (2006.01)

(52) U.S. Cl.
USPC .......................................... 356/445; 359/642

(58) Field of Classification Search
USPC ........... 356/445, 121, 246; 250/458.1, 459, 1, 250/339, 201.9; 359/277, 642, 619, 725
See application file for complete search history.

(56) References Cited

U.S. PATENT DOCUMENTS

| | | | | |
|---|---|---|---|---|
| 5,233,174 A | * | 8/1993 | Zmek | 250/201.9 |
| 5,291,334 A | | 3/1994 | Wirth | |
| 5,493,391 A | * | 2/1996 | Neal et al. | 356/121 |
| 5,629,765 A | * | 5/1997 | Schmutz | 356/121 |
| 6,184,974 B1 | * | 2/2001 | Neal et al. | 356/121 |
| 6,376,819 B1 | | 4/2002 | Neal | |
| 6,437,345 B1 | * | 8/2002 | Bruno-Raimondi et al. | 250/458.1 |
| 7,084,966 B2 | * | 8/2006 | Zaidi | 356/237.2 |
| 7,158,224 B2 | | 1/2007 | Montagu | |
| 7,286,295 B1 | | 10/2007 | Sweatt | |
| 8,119,995 B2 | * | 2/2012 | Klunder et al. | 250/458.1 |
| 8,358,366 B1 | * | 1/2013 | Georgiev | 348/335 |
| 2005/0084912 A1 | * | 4/2005 | Poponin | 435/7.1 |
| 2007/0247698 A1 | * | 10/2007 | Yoon | 359/277 |
| 2010/0123873 A1 | * | 5/2010 | Raymond et al. | 351/212 |
| 2010/0267163 A1 | * | 10/2010 | Ran et al. | 436/164 |

FOREIGN PATENT DOCUMENTS

| | | |
|---|---|---|
| JP | 2004317376 A1 | 11/2004 |
| WO | 2007039852 A1 | 4/2007 |
| WO | 2008155716 A1 | 12/2008 |

* cited by examiner

*Primary Examiner* — Sang Nguyen

(57) ABSTRACT

The invention relates to focusing optics (100) for a biosensor (10) which allow with simple means to accurately image an extended investigation region (13) onto a detector plane (P). To this end, the focusing optics (100) comprises at least two focusing lenslets (LL) that are arranged adjacent to each other such that they image an incident parallel light beam (L2) that is directed along a main optical axis (MOA) onto a common plane (P). The output light beam (L2) that is received by the focusing optics (100) may preferably originate from total internal reflection of a parallel input light beam (L1) at the investigation region (13) of a transparent carrier.

14 Claims, 4 Drawing Sheets

OPTICAL BIOSENSOR WITH FOCUSING OPTICS

FIELD OF THE INVENTION

The invention relates to focusing optics for an optical biosensor, to a biosensor comprising such optics, and to a method for imaging an investigation region onto the detector plane of a light detector.

BACKGROUND OF THE INVENTION

The WO 2008/155716 discloses an optical biosensor in which an input light beam is totally internally reflected and the resulting output light beam is detected and evaluated with respect to the amount of target components at the reflection surface. When a plurality of analytes shall be tested in parallel in such or a similar biosensor, it is often necessary to provide the sample in spatially separated chambers. This increases the field of view that has to be surveyed, leading either to image deteriorations at the periphery of the imaged area or to complex optical systems.

SUMMARY OF THE INVENTION

Based on this situation it was an object of the present invention to provide means that allow the simultaneous detection of analytes in several distinct sample chambers of an optical biosensor.

This object is achieved by focusing optics according to claim 1, an optical biosensor according to claim 2, a method according to claim 3, and a use according to claim 15. Preferred embodiments are disclosed in the dependent claims.

According to its first aspect, the invention relates to focusing optics for an optical bio sensor, said optics comprising at least two focusing lenslets that are arranged adjacent to each other such that they image an incident parallel light beam, which is directed along a main optical axis of the focusing optics, onto a common plane.

The term "lenslet" is used in this context to denote a lens that basically corresponds to a conventional optical lens, however with a size that is comparatively small. More precisely, the size of such a lenslet shall be smaller than the diameter of a light beam which shall be processed by the optics. Processing of the complete light beam hence requires the application of an array of lenslets. Preferably, the individual lenslets are fixed with respect to each other, for example by attachment to a common frame. The focusing optics can then be handled as a single object. The "main optical axis" is used to characterize the geometry of the focusing optics. Usually, this main optical axis corresponds to a symmetry axis of the focusing optics and/or it is parallel to the individual optical axes of the lenslets on the object side. In many cases the main optical axis corresponds to the mean of all individual optical axes. The "optical axis" of a refractive optical element is as usually defined as a direction along which there is some degree of rotational symmetry of the element (and, consequently, of its optical behavior). Moreover, the term "object side" is used to denote one side of a lenslet and of the complete focusing optics; during application, an object will typically be disposed on the "object side" of the focusing optics, while its image is generated at the opposite side, which is consequently called "image side".

According to its second aspect, the invention relates to an optical biosensor comprising the following components:

a) Means for generating a substantially parallel "output light beam" that emanates from an investigation region and that is directed along an axis called "main optical axis". The investigation region will typically be a sub-region of some surface that can be contacted by a sample, wherein evaluation of an image of the investigation region will yield some information about said sample.

b) A light detector with a light sensitive detector plane. The light detector may comprise any suitable sensor or plurality of sensors by which light of a given spectrum can be detected, for example photodiodes, photo resistors, photocells, a CCD/CMOS chip, or a photo multiplier tube.

c) Focusing optics comprising at least two focusing lenslets that are arranged adjacent to each other for focusing said output light beam onto the detector plane. With other words, the focusing optics of the optical biosensor is a focusing optics according to the first aspect of the invention with its object side being oriented towards the investigation region.

According to a third aspect, the invention relates to a method for imaging an investigation region onto the detector plane of a light detector of an optical biosensor, said method comprising the following steps:

a) Generating a substantially parallel output light beam that emanates from the investigation region and propagates along an axis called "main optical axis".

b) Focusing adjacent sub-beams of the aforementioned output light beam separately by lenslets of a focusing optics onto the detector plane.

The focusing optics, the optical bio sensor, and the method according to the above aspects of the invention have in common to allow the focusing of several sub-beams of a large parallel output light beam onto different zones of a detector plane. An output light beam with a large diameter can hence be processed while at the same time optical distortions in peripheral areas are avoided because processing is done with respect to sub-beams of limited extension. This allows to survey a comparatively large investigation region of an optical bio sensor with a high accuracy of the optical measurements but without a complex optical system that might be difficult to adjust. Instead, the focusing optics comprising a plurality of lenslets arranged adjacent to each other suffices.

In the following, further developments of the invention will be described that relate to the focusing optics, the optical biosensor, and the method according to the above aspects of the present invention.

The parallel output light beam that emanates from the investigation region and that is processed by the focusing optics may in general be generated in many different ways, for example by transmission of light through the investigation region. In a preferred embodiment of the invention, the output light beam is generated by total internal reflection of an input light beam at the investigation region. The input light beam can be generated by a light source of the optical biosensor, for example a laser or a light emitting diode (LED), optionally provided with some optics for shaping and directing the input light beam.

The light detector preferably comprises a plurality of individual detector units, which will as usually be called "pixels" in the following. Such a pixilated light detector may particularly be realized by an image sensor, for example a CCD or CMOS device as it is known from digital cameras. A plurality of detector pixels allows to evaluate the information comprised by the output light beam in a spatially resolved way with respect to the investigation region.

According to another embodiment, the biosensor comprises an image processing device, for example a computer with associated software for digital image processing, said image processing device being able to process images generated by different lenslets. In particularly, the image processing device may be adapted to combine images generated by different lenslets. This approach is useful if the individual images generated by different lenslets are separated from each other in the detector plane by borders which comprise no useful information. The areas of the detector plane comprising valid images can then be isolated and stitched together by the image processing device.

The investigation region may preferably cover a plurality of physically separated sample chambers, called "wells", that can separately provide samples. Such wells may for example be realized on the surface of a (transparent) carrier. The provision of separated wells allows to prepare one or more samples under different conditions and to evaluate these preparations in parallel. The plurality of separated wells typically implies a comparatively large, elongated shape of the investigation region. Nevertheless, this investigation region can accurately be imaged onto the detector plane with the help of the focusing optics.

Focusing optics with the required imaging characteristics (i.e. imaging a parallel beam onto a common plane) can for example be realized by lenslets with their individual optical axes being parallel on the object side.

In order to avoid a mutual overlap of the images generated by the different lenslets, the magnification M of the lenslets is preferably chosen to be smaller than one, i.e. |M|<1. It should however be noted that also cases in which the magnification is larger than 1 will work, though some parts of the images will then be rendered useless due to an overlap (this may be tolerable if the sample chamber is appropriately designed).

In a preferred embodiment of the invention, the image generated by at least one lenslet is shifted (with respect to an extension of its individual optical axis from the object to the image side) towards a selected axis. In case the lenslets have a magnification smaller than one, "useless" borders around the images generated by the individual lenslets can be avoided by shifting these images in the detector plane towards the mentioned selected axis. The selected axis will often be chosen to correspond to the main optical axis of the focusing optics.

The aforementioned shift of the lenslet images can be realized in different ways. According to a first approach, it is achieved by making the individual optical axes of the lenslets on the image side of the focusing optics convergence (towards the selected axis). In this context, the "individual optical axis on the image side of a lenslet" is defined by the image-side path of a light ray that comes along the individual optical axis on the object side of the lenslet.

According to another embodiment of the invention, the (preferably planar) facet of at least one lenslet on the image side is tilted with respect to the main optical axis. This implies that the aforementioned individual optical axis of said lenslet on its image side is also tilted, which allows to shift the image generated by the lenslet in the detector plane.

According to a further development of the aforementioned embodiment, a plurality of lenslets has such tilted surfaces on their image side, wherein the tilting angle increases with the distance of the lenslet from a selected axis (e.g. from the main optical axis of the focusing optics). With this embodiment, convergent individual optical axes of the lenslets on the image side can be realized, and hence the shifting of the lenslet images towards the selected axis.

According to another embodiment of the invention, at least one lenslet is off-centre with respect to the sub-beam of the output light beam which this lenslet is exposed to. This means that the individual optical axis of this lenslet does not coincide with the middle axis of said sub-beam. With a plurality of such off-centre lenslets, convergence of the lenslet images towards a selected axis can be realized.

The invention further relates to the use of the focusing optics for the biosensor described above for molecular diagnostics, biological sample analysis, or chemical sample analysis, food analysis, and/or forensic analysis. Molecular diagnostics may for example be accomplished with the help of magnetic beads or fluorescent particles that are directly or indirectly attached to target molecules.

BRIEF DESCRIPTION OF THE DRAWINGS

These and other aspects of the invention will be apparent from and elucidated with reference to the embodiment(s) described hereinafter. These embodiments will be described by way of example with the help of the accompanying drawings in which.

Like reference numbers or numbers differing by integer multiples of 100 refer in the Figures to identical or similar components.

DESCRIPTION OF PREFERRED EMBODIMENTS

Though the present invention will in the following be described with respect to a particular setup (using magnetic particles and frustrated total internal reflection as measurement principle), it is not limited to such an approach and can favorably be used in many different applications and setups.

Figure 1A:
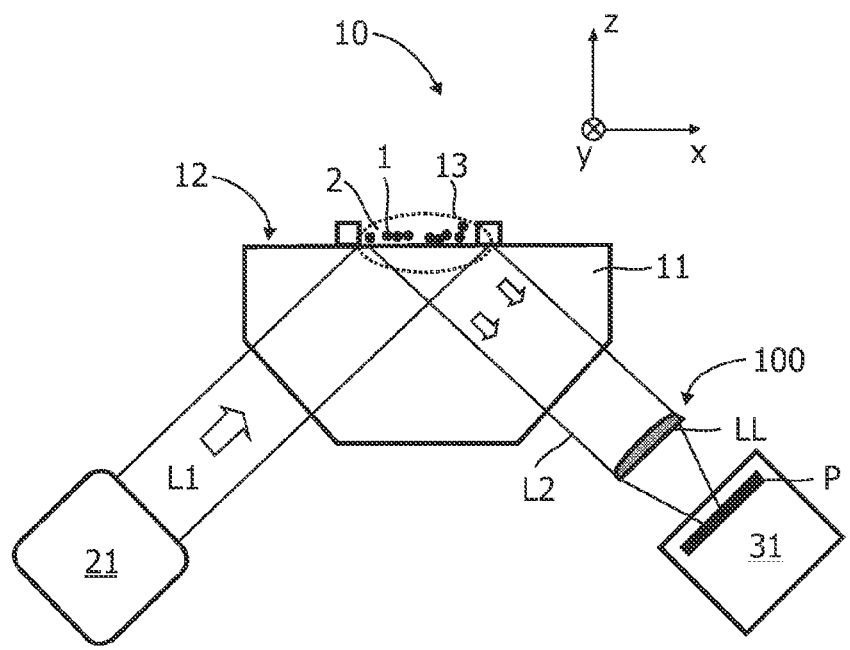
FIG. 1a schematically illustrates an optical biosensor according to the present invention in a side view.
Figure 1B:
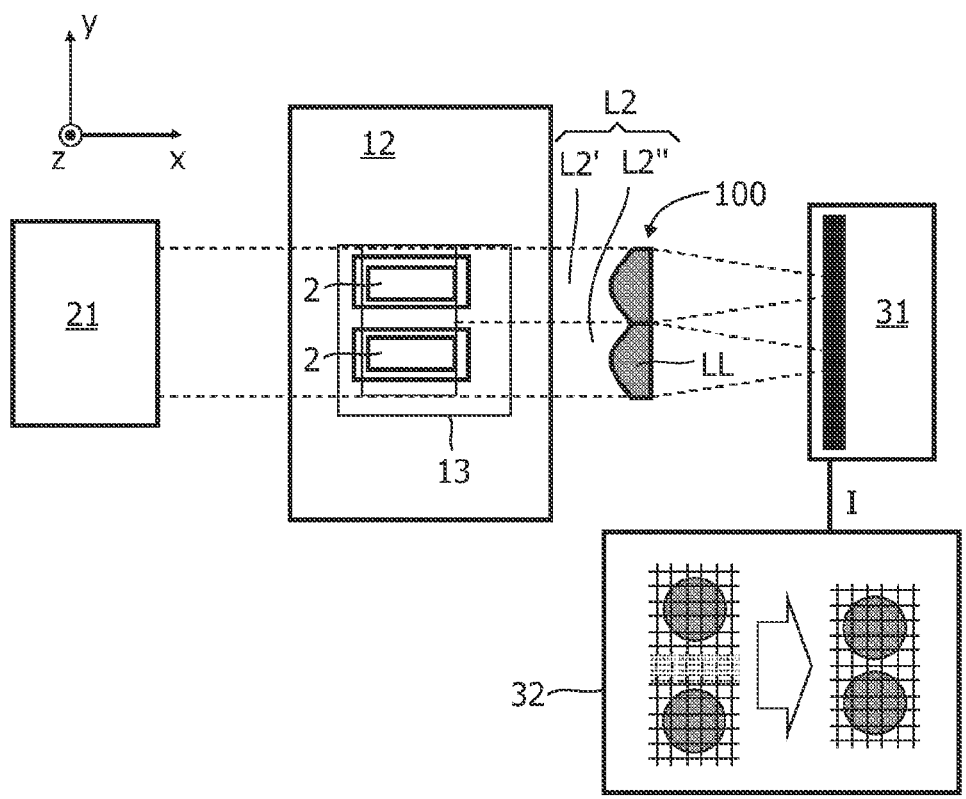
FIG. 1b shows the biosensor of FIG. 1a in a top view.

FIGS. 1a and 1b show a general setup with of an optical biosensor 10 according to the present invention in a side view and a top view, respectively. The biosensor 10 setup comprises a carrier 11 that may for example be made from glass or transparent plastic like polystyrene. The carrier 11 comprises on its upper "contact surface" 12 a plurality of physically separated sample chambers or wells 2 in which sample fluids with target components to be detected (e.g. drugs, antibodies, DNA, etc.) can be provided. The samples further comprise magnetic particles, for example superparamagnetic beads, wherein these particles are usually bound (via e.g. a coating with antibodies) as labels to the aforementioned target components. For simplicity only the combination of target components and magnetic particles is shown in the Figures and will be called "target particle 1" in the following. It should be noted that instead of magnetic particles other label particles, for example electrically charged or fluorescent particles, could be used as well. The interface between the carrier 11 and the wells 2 is usually coated with capture elements, e.g. antibodies, which can specifically bind to target particles.

The sensor device may preferably comprise a magnetic field generator (not shown), for example an electromagnet with a coil and a core, for controllably generating a magnetic field at the contact surface 12 and in the adjacent space of the wells 2. With the help of this magnetic field, the target particles 1 can be manipulated, i.e. be magnetized and particularly be moved (if magnetic fields with gradients are used). Thus it is for example possible to attract target particles 1 to the contact surface 12 in order to accelerate their binding to said surface, or to wash unbound target particles away from the contact surface before a measurement.

The sensor device further comprises a light source 21 that generates an input light beam L1 which is transmitted into the carrier 11 through an "entrance window". As light source 21, e.g. a commercial CD ($\lambda=780$ nm), DVD ($\lambda=658$ nm), or BD ($\lambda=405$ nm) laser-diode, or a collimated LED source can be used. A collimator lens may be used to make the input light beam L1 parallel, and a pinhole may be used to control the beam diameter. The input light beam L1 arrives in an investigation region 13 of the contact surface 12 at an angle larger than the critical angle $\theta_c$ of total internal reflection (TIR) and is therefore totally internally reflected in an "output light beam" L2. The output light beam L2 leaves the carrier 11 through another surface ("exit window") and is detected by a light detector 31. The light detector 31 determines the amount of light of the output light beam L2 (e.g. expressed by the light intensity of this light beam in the whole spectrum or a certain part of the spectrum). In the shown embodiment, this is done with the help of a detector plane P onto which the investigation region 13 is imaged. The detected image signals I are evaluated and optionally monitored over an observation period by an evaluation and recording module 32 that is coupled to the detector 31.

The described optical biosensor applies optical means for the detection of target particles 1. For eliminating or at least minimizing the influence of background (e.g. of the sample fluid, such as saliva, blood, etc.), the detection technique should be surface-specific. As indicated above, this is achieved by using the principle of frustrated total internal reflection (FTIR). This principle is based on the fact that an evanescent wave penetrates (exponentially dropping in intensity) into the sample chambers 2 when the incident light beam L1 is totally internally reflected. If this evanescent wave then interacts with another medium like the bound target particles 1, part of the input light will be coupled into the sample fluid (this is called "frustrated total internal reflection"), and the reflected intensity will be reduced (while the reflected intensity will be 100% for a clean interface and no interaction). Depending on the amount of disturbance, i.e. the amount of target particles on or very near (within about 200 nm) to the TIR surface (not in the rest of the sample chambers 2), the reflected intensity will drop accordingly. This intensity drop is a direct measure for the amount of bound target particles 1, and therefore for the concentration of target particles in the sample. For the materials of a typical application, medium A of the carrier 11 can be glass and/or some transparent plastic with a typical refractive index of 1.52 or larger. Medium B in the sample chambers 2 will be water-based and have a refractive index close to 1.3. This corresponds to a critical angle $\theta_c$ of 60°.

Advantages of the described optical read-out combined with magnetic labels for actuation are the following:
- Cheap cartridge: The carrier 11 can consist of a relatively simple, injection-molded piece of polymer material.
- Actuation and sensing are orthogonal: Magnetic actuation of the target particles (by large magnetic fields and magnetic field gradients) does not influence the sensing process. The optical method therefore allows a continuous monitoring of the signal during actuation. This provides a lot of insights into the assay process and it allows easy kinetic detection methods based on signal slopes.
- Large multiplexing possibilities for multi-analyte testing: The contact surface 12 in a disposable cartridge can be optically scanned over a large area. Alternatively, large-area imaging is possible allowing a large detection array. Such an array (located on an optical transparent surface) can be made by e.g. ink-jet printing of different binding molecules on the optical surface.
- The method also enables high-throughput testing in (specifically designed) well-plates by using multiple beams and multiple detectors and multiple actuation magnets (either mechanically moved or electro-magnetically actuated).

Some applications of the described bio sensor are the detection of a heart attack or the use of drugs-of-abuse. By binding or non-binding of the magnetic beads to the contact surface in a biological assay, multiple bio-markers can be detected in e.g. saliva or human blood plasma. By using (frustrated) total internal reflection as a detection technique in combination with magnetic actuated beads, very low detection limits (in the pM range and even less) are achieved in combination with short measurement/assay times. However, if multiple bio-assays would be run at the same time, problems can occur when detecting specific bio-markers simultaneously in one single reaction chamber. Some biological assays show interference when run at the same time. Also the optimal reaction conditions per assay may vary, e.g. pH, usage of salts, sugars, specific buffer components etc. Therefore, it is required in some cases that each assay runs in its own reaction chamber or well 2, as shown in FIG. 1.

As the wells 2 need to have walls to confine the liquids, buffers etc., much more space is needed at the sensor surface to accommodate all bio-assays separately. This means that the sensor surface of the investigation region 13 that has to be imaged increases. Due to the chosen geometry of the optical plane, it is the easiest to extend the sensor surface along the length of the optical plane (y-direction in FIG. 1), i.e. the investigation region 13 becomes asymmetric and very elongated in only one direction. This has severe consequences for the imaging system, as a much "longer" field of view is needed, while maintaining compact optics.

In practical realizations of the biosensor 10, the investigation region 13 is imaged onto a CCD/CMOS camera using an imaging lens. A clear image can be obtained using a single cheap replicated collimator lens for an object size of about $2\times1$ mm$^2$. As explained above, there is a need to increase the object size to a more elongated area with typical dimensions of $6.5\times1$ mm$^2$ or even larger. As a result a larger field needs to be imaged by the image lens, and optical aberrations will partially destroy the image quality. This can be overcome by a more complex lens design, using more than one lens element. A disadvantage of this method is the increased cost of manufacturing since these individual lens elements need to be precisely aligned with respect to each other during the manufacturing process and multiple optical components are needed.

To overcome the described problems, it is proposed here to use only a single lens element, consisting of a series of smaller lenslets. This lenslet array can for instance be produced using standard plastic injection moulding techniques. As a result the proposed method uses only one single lens element and only requires course alignment for correct image focusing.

It should be noted that the method can reasonably be applied only in imaging systems where the light beam originating from the object is a well-collimated, substantially parallel beam. For the application shown in FIG. 1, this is the case as the object is being imaged by total internal reflection (and not by for instance scattering) of a parallel input light beam L1, giving rise to a parallel output light beam L2 reaching the imaging lens. In technical terms: the object space numerical aperture is virtually zero in the biosensor application since the illumination is done using a well-collimated beam from a light source 21.

Hence the main operation principle of the proposed solution is a sub-division of the main object (investigation region 13) into smaller sub-objects with corresponding sub-beams L2', L2'' of the output light beam L2, thereby imaging each sub-object using a single lenslet LL, being part of a lenslet array or focusing optics 100. The result is a series of sub-images on the detector plane P that can be stitched into one single image using standard and simple image processing techniques in the image processing device 32.

Figure 2:
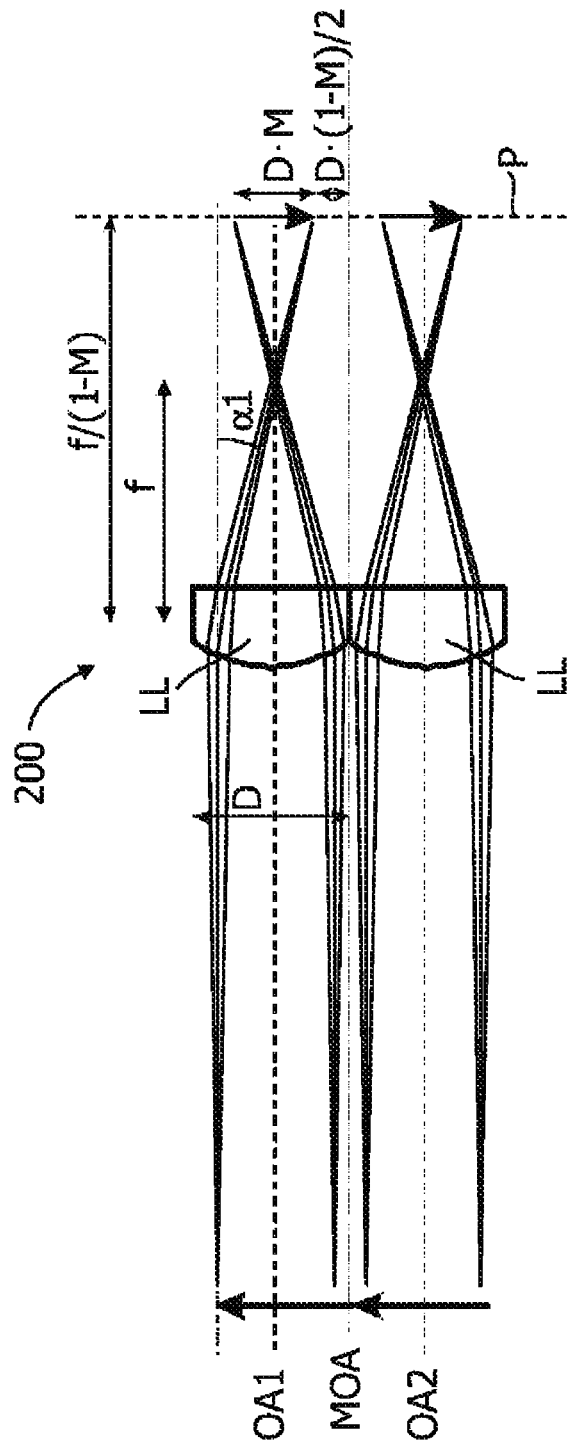
FIG. 2 illustrates an embodiment of focusing optics comprising two adjacent lenslets.

FIG. 2 illustrates the operation principle for a special focusing optics 200 comprising two (identical) lenslets LL arranged adjacent to each other. The lenslets LL have a diameter D, a focal length f, and individual optical axes OA1, OA2 (on the object side, i.e. left side in FIG. 2) which are parallel to each other and to the main optical axis MOA of the whole focusing optics 200. As usual, the individual optical axes OA1, OA2 are axes of rotational symmetry of the respective lenslets LL. Aberrations are minimized at the edges of the main image by a reduction of the maximum field angle (due to splitting up the object and imaging the sub-objects individually by separate lens elements).

The proposed method works as long as the object space numerical aperture (NA) is virtually zero, i.e. light originating from a single sub-object is allowed to be imaged by only one lenslet LL. Otherwise multiple images of a single sub-object would be imaged onto the detector plane P, making the imaging useless.

It should further be noted that there is an empty space or border between to sub-images. This empty space defines an upper limit for the magnification M that can be used given a finite dimension of the detector plane P. Obviously, the magnification M of the lenslets should be smaller than 1 ($|M|<1$) to prevent that two images overlap.

In a general situation, the total object size is given by $H_{obj}$, the number of lenslets LL to be used is N>2, the magnification is given by M ($-1<M<0$), and the detector size is $H_{det}$. Two procedures are then possible:

1. Stitching the digitalized images I in software using image processing. The upper limit of the magnification is then given by $|M|_{max}$ with $-|M|_{max}<M<0$ and:

$$|M|_{max} = \frac{N \cdot H_{det} - (N-1) \cdot H_{obj}}{(2N-1) \cdot H_{obj}}$$

2. Shifting the sub-images towards the main optical axis using imaging optics. In this case the full sensor surface can be used and the maximum magnification is then simply given by:

$$|M|_{max} = H_{det}/H_{obj}$$

These procedures will now be described in more detail, starting with the stitching of sub-images. On the detector plane P, an array of sub-images of width D·M is formed by the lenslet array 200, as illustrated in FIG. 2. These sub-images may be stitched together by using known image processing techniques. The actually used sensor area is in this case larger than the net image area, due to the empty spaces in between the sub-images. As a result the optical magnification M that can be used is limited.

In the second procedure, the respective sub-images may be shifted in the detector plane P such that the empty spaces between them are reduced to a minimum in order to allow for a larger magnification M. This can be done in the optical domain using two approaches:

2A. Using lenslets LL centered with respect to the center of the sub-objects, but having a tilted second surface where the tilt angle of the slanted sub-surfaces increases when going away from the main optical axis of the lenslet array (cf. FIGS. 3, 4).

Figure 5:
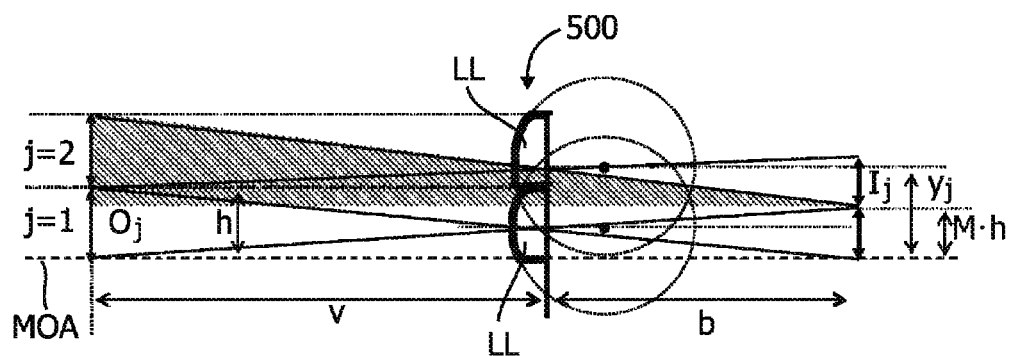
FIG. 5 illustrates an embodiment of focusing optics with off-centred lenslets.

2B. Using lenslets LL off-centered with respect to the center of the sub-objects (FIG. 5).

Figure 3:
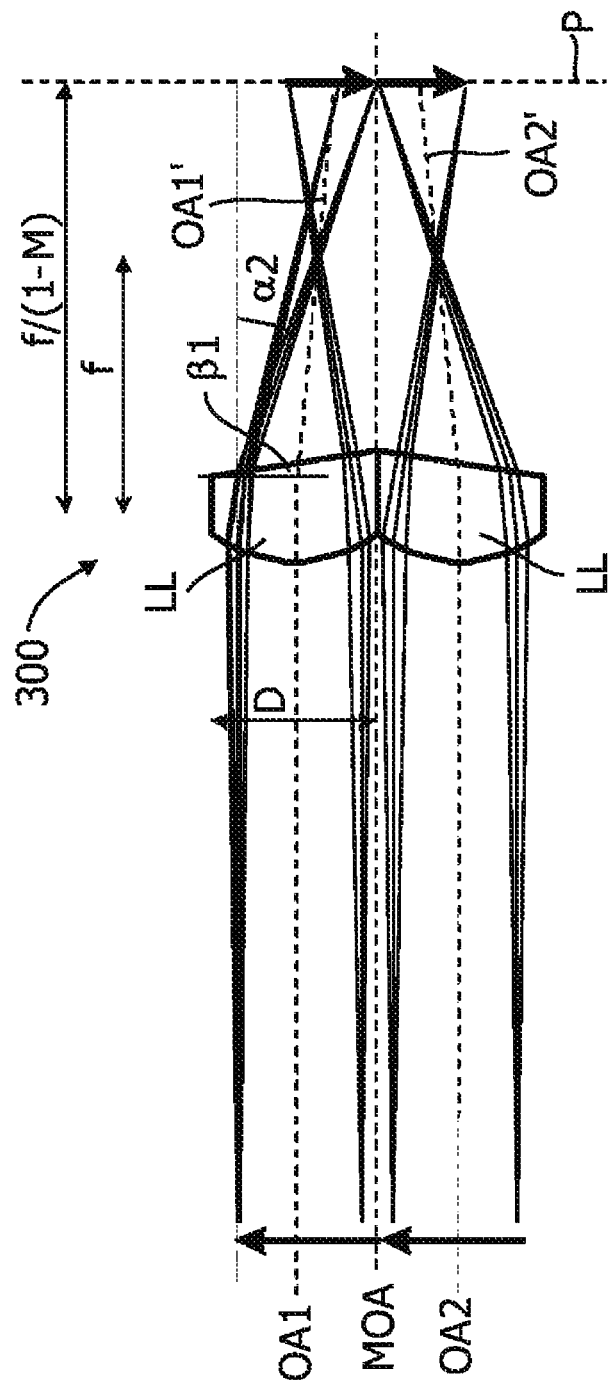
FIG. 3 illustrates an embodiment of focusing optics comprising two adjacent lenslets with slanted surfaces on the image side.
Figure 4:
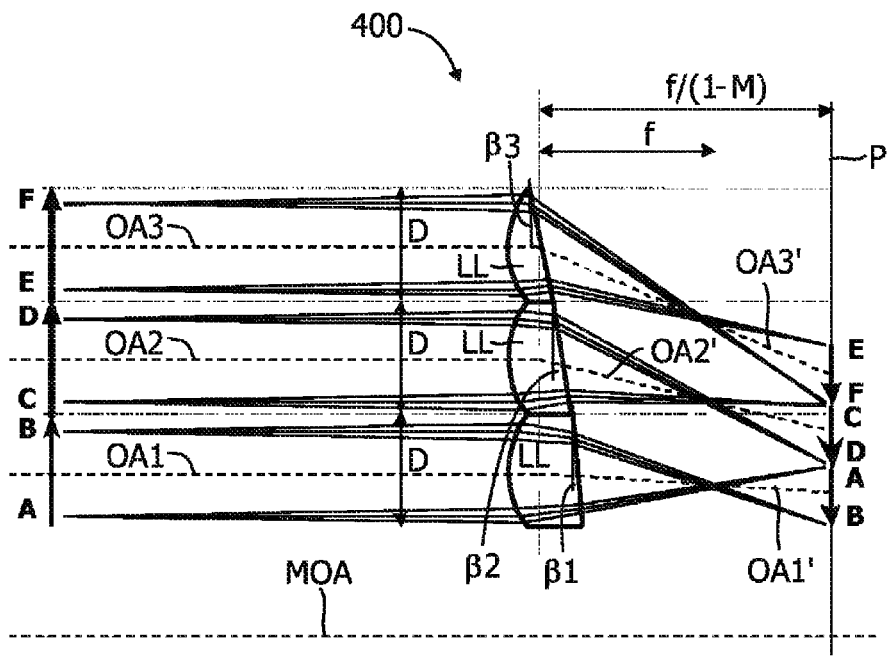
FIG. 4 illustrates an embodiment of focusing optics comprising three lenslets having differently slanted surfaces on the image side.

FIGS. 3 and 4 show the first approach 2A (lenslet arrays having tilted surfaces) for focusing optics 300 and 400 with two and three lenslets, respectively. The object to be imaged by the lenslet arrays may be considered as a series of sub-objects, each individually being imaged by a single lenslet of the array at image distance b:

$$1/b = 1/f - 1/v = 1/f + M/b \Rightarrow b = f(1-M)$$

Each sub-object is imaged with a magnification smaller than 1 in order to prevent the sub-images to overlap. Consequently, there is an empty space between each sub-image, making the full image span unnecessarily larger than required. In order to get rid of these empty spaces in the image, the lens array may be equipped with slightly tilted surfaces, refracting the sub-image towards the optical axis. This is tantamount to saying that the individual optical axes OA1', OA2', OA3' of the lenslets LL on the image side converge, wherein these axes are defined by the path of a light ray propagating along the (individual and main) optical axes OA1, OA2, OA3, MOA on the object side.

The amount of tilt (angles $\beta1$, $\beta2$, $\beta3$) to be introduced for each sub-image depends on the position of the sub-image with respect to the main optical axis MOA and on the magnification M. For each sub-image j the required tilt angle $\beta j$ of the lens surface may be calculated as follows (wherein j=0 corresponds with the sub-image closest to the main optical axis MOA; when going to the outer rim of the object/lens array, j increases with 1 for each subsequent lenslet):

The sub-object width is D. The magnification $|M|$ of the lenslets LL is smaller than 1, resulting in a series of sub-images with size $D \cdot |M|$, separated from each other over a distance D. Consequently there is an empty space between each sub-image of width $D \cdot (1-|M|)$. In order to make a single closed image, all sub-images have to be shifted towards the main optical axis MOA. For the first sub-image the shift angle $\Delta \alpha_1$ is calculated as follows:

$$\tan(\alpha_1) = 1/2 D(1+|M|) / [f \cdot (1-M)]$$
$$= \frac{D}{2f} \cdot \frac{1+|M|}{1-M}$$
$$= NA_{lenslet} \cdot \frac{1+|M|}{1-M}$$

$$\tan(\alpha_2) = D/[f \cdot (1-M)] = \frac{D}{2f} \cdot 2 \frac{1}{1-M} = NA_{lenslet} \cdot \frac{2}{1-M}$$

$$\Delta \alpha_1 = \alpha_2 - \alpha_1$$
$$= NA_{lenslet} \cdot \left[\frac{2}{1-M} - \frac{1+|M|}{1-M}\right]$$
$$= NA_{lenslet} \cdot \left[\frac{1-m}{1+m}\right];$$

-continued $$m = |M|;$$
$$M < 0$$

Of course the same method can be used for making larger subdivision of the main image. Sub-images further away from the main optical axis should be shifted over a larger angle towards the optical axis. As long as the small-angle approximation is valid, this shift for the other sub-images is equal to:

$$\Delta\alpha_j = (2j-1)\cdot\Delta\alpha_1; j\geq 1$$

This lateral shift of the sub-images can be obtained by slightly tilting the lenslets' facets on the image side, such that it acts as a wedge, with a ray deviation of $$\Delta\alpha_{wedge} = (n-1)\cdot\beta$$

(again for small angles $\Delta\alpha$ and $\beta$, with n being the refractive index of the lens material). For the different sub-images an array of wedge-like structures can be incorporated in the lens array, each having a wedge-angle $\beta$. This results in a prescription for the tilt angles $\beta_j$ of the respective lenslets LL of the focusing system 400 (FIG. 4) according to:

$$\beta_j(\text{radians}) = \Delta\alpha_j / (n-1) = NA_{lenslet} \cdot \frac{(1-m)(2j-1)}{(m+1)(n-1)}; j \geq 1$$

FIG. 5 illustrates the second approach 2B (off-centered lenslets) for shifting the sub-images towards the main optical axis MOA. Here off-centered lenslets LL are used in the focusing optics 500, where the individual optical axes of the individual lenslets is offset with respect to the center of their sub-objects Oj (or sub-beams L2', L2", respectively). The required tilt that was introduced by the slanted surfaces in the previous method is now incorporated in the imaging of the lenslets, where each sub-object Oj is imaged having an offset with respect to the optical axis OAj' of the corresponding lenslet LL. In FIG. 5, the position of the individual optical axes OA1', OA2' of the respective lenslets LL is given by $y_j$. Here the magnification is M, and the size of each sub-object is given by $h = H_{obj}/N$.

From geometry considerations using the hatched triangle in FIG. 5 one can deduce:

$$y_j = \frac{b}{b+v}[j\cdot h - (j-1)\cdot|M|\cdot h] + (j-1)\cdot|M|\cdot h$$

This leads to the following equation for $y_j$, giving the position of the optical axis of each lenslet with respect to the central main optical axis MOA of the lenslet array:

$$y_j = \frac{M \cdot h \cdot (2j-1)}{M-1} = \frac{M \cdot H_{obj} \cdot (2j-1)}{(M-1)\cdot N}$$

It should be noted that j>1 in this equation. Since the lenslet array is symmetrical with respect to the main optical axis MOA the equation can be rewritten as:

$$y_j = \text{sign}(j) \cdot \frac{M \cdot h \cdot (2|j|-1)}{M-1} = \frac{M \cdot H_{obj} \cdot (2|j|-1)}{(M-1)\cdot N};$$
$$j = \pm 1, \pm 2, \ldots$$

While the invention was described above with reference to particular embodiments, various modifications and extensions are possible, for example:

Molecular targets often determine the concentration and/or presence of larger moieties, e.g. cells, viruses, or fractions of cells or viruses, tissue extract, etc.

In addition to molecular assays, also larger moieties can be detected with sensor devices according to the invention, e.g. cells, viruses, or fractions of cells or viruses, tissue extract, etc.

The detection can occur with or without scanning of the sensor element with respect to the sensor surface.

Measurement data can be derived as an end-point measurement, as well as by recording signals kinetically or intermittently.

The particles serving as labels can be detected directly by the sensing method. As well, the particles can be further processed prior to detection. An example of further processing is that materials are added or that the (bio) chemical or physical properties of the label are modified to facilitate detection.

The device and method can be used with several biochemical assay types, e.g. binding/unbinding assay, sandwich assay, competition assay, displacement assay, enzymatic assay, etc. It is especially suitable for DNA detection because large scale multiplexing is easily possible and different oligos can be spotted via ink-jet printing on a substrate.

The device and method are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device and method can be used as rapid, robust, and easy to use point-of-care biosensors for small sample volumes. The reaction chamber can be a disposable item to be used with a compact reader, containing the one or more field generating means and one or more detection means. Also, the device, methods and systems of the present invention can be used in automated high-throughput testing. In this case, the reaction chamber is e.g. a well-plate or cuvette, fitting into an automated instrument.

With nano-particles are meant particles having at least one dimension ranging between 3 nm and 5000 nm, preferably between 10 nm and 3000 nm, more preferred between 50 nm and 1000 nm.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:
1. An optical biosensor, comprising:
a) a light source and an investigation region defining a plurality of sample chambers for generating a substantially parallel output light beam including a sub beam emanating from each sample chamber and that is directed along a main optical axis;

b) a light detector with a detector plane;

c) focusing optics including a focusing lenslet corresponding to each sub-beam for focusing each of the sub-beams of the output light beam onto the detector plane to generate a sub-image of a corresponding sample chamber on the detector plane, each focusing lenslet being configured to maximize a size of the corresponding sample chamber sub-image on the detector plane.

2. The optical biosensor according to claim 1, wherein the output light sub-beams are generated by frustrated total internal reflection of an input light beam at the sample chambers.

3. The optical biosensor according to claim 1, wherein the detector plane includes a CCD/CMOS camera having an array of detector pixels.

4. The optical biosensor according to claim 1, wherein each sample chamber sub-image has a width D·M and are separated from each other by D·(1−M), where D is a size of the corresponding sample chamber and M is a magnification of a corresponding lenslet and further including:

an image processing device for electronically stitching the sample chamber sub-images together; and wherein the magnification of each lenslet is:

$$|M|=N \cdot H_{det}-(N-1) \cdot H_{obj}/(2N-1) \cdot H_{obj}$$

where N is a number of lenslets, $H_{det}$ is a size of the detector, and $H_{obj}$ is a size of the sample chambers on the contact surface.

5. The optical biosensor according to claim 1, wherein the contact surface includes a plurality of sample chambers each configured to receive a sample.

6. The optical biosensor according to claim 1, wherein the sub-beams travel along parallel individual optical axes between the contact surface and the lenslets, an object space numerical aperture is virtually zero, and each of the lenslets has a magnification smaller than one.

7. The optical biosensor according to claim 1, wherein there are a plurality of adjacent sampling chambers with a space between each sampling chamber and the lenslets are configured to shift the sample chamber sub-images toward each other to reduce empty spaces between the sample chamber sub-images to a minimum such that the magnetization of the lenslets is maximized.

8. The optical biosensor according to claim 7, wherein a magnetization M of each lenslet is:

$$M=H_{det}/H_{obj},$$

where $H_{det}$ is a size of the detector plane and $H_{obj}$ is a size spanned by the sample chambers.

9. The optical biosensor according to claim 8, wherein the lenslets refract the sub-beams of the output light beam along converging individual optical axes between the lenslets and the detector plane.

10. The optical biosensor according to claim 7, wherein each of the lenslets has a facet on its detector plane side which is tilted with respect to the main optical axis such that the sample chamber images on the detector plane are shifted toward each other.

11. The optical biosensor according to claim 10, wherein a tilting angle of the facets increases with distance of the lenslets from a main optical axis.

12. The optical biosensor according to claim 7, wherein at least one lenslet is off-center with respect to the corresponding sub-beam of the output light beam such that the corresponding sample chamber sub-image is shifted toward the main optical axis and to minimize empty space between sample chamber sub-images.

13. Use of the optical biosensor according to claim 1 for molecular diagnostics, biological sample analysis, chemical sample analysis, food analysis, and/or forensic analysis.

14. A method for imaging an investigation region onto a detector plane of a light detector, said method comprising the following steps:

a) generating an array of substantially parallel output light sub-beams that emanates from one of an array of sample chambers in the investigation region parallel to a main optical axis, each sub-beam emanating from a corresponding one of the sample chambers;

b) focusing adjacent sub-beams of the output light beam separately by corresponding lenslets of focusing optics into a sub-image of a corresponding sample chamber onto the detector plane, with the lenslets magnifying and shifting sample chamber sub-images toward the main optical axis to reduce empty space between the sample chamber sub-images to a minimum.

* * * * *